United States Patent
Chien

(10) Patent No.: US 10,602,967 B2
(45) Date of Patent: Mar. 31, 2020

(54) OPHTHALMIC LENS WITH GLUCOSE SENSITIVE PAD AND METHOD FOR MANUFACTURING SAME

(71) Applicant: SCIENBIZIP CONSULTING(SHENZHEN)CO., LTD., Shenzhen (CN)

(72) Inventor: Hsiu-Wen Chien, Tu-Cheng (TW)

(73) Assignee: ScienBiziP Consulting(Shenzhen)Co., Ltd., Shenzhen (CN)

( * ) Notice: Subject to any disclaimer, the term of this patent is extended or adjusted under 35 U.S.C. 154(b) by 291 days.

(21) Appl. No.: 15/674,732

(22) Filed: Aug. 11, 2017

(65) Prior Publication Data

US 2019/0000359 A1    Jan. 3, 2019

(30) Foreign Application Priority Data

Jun. 30, 2017   (TW) ................. 106121876

(51) Int. Cl.
*A61B 5/00*     (2006.01)
*A61B 5/145*    (2006.01)
(Continued)

(52) U.S. Cl.
CPC ........ *A61B 5/14532* (2013.01); *A61B 5/1468* (2013.01); *A61B 5/14507* (2013.01); *A61B 5/6821* (2013.01); *A61B 10/0045* (2013.01); *B29B 13/08* (2013.01); *B29D 11/00048* (2013.01); *G02B 1/041* (2013.01); *G02B 1/043* (2013.01); *G02C 7/04* (2013.01); *G02C 11/00* (2013.01); *A61B 2010/0067* (2013.01);
(Continued)

(58) Field of Classification Search
CPC ........... A61B 5/145; A61B 10/00; A61B 5/00; A61B 5/1468; A61B 5/14532; A61B 5/6821; A61B 5/14507; A61B 10/0045; A61B 2562/0295; A61B 2562/12; A61B 2010/006; B29B 13/08; B29D 11/00; B29D 11/00048; B29D 11/00134; G02B 1/04; G02B 1/041; G02B 1/043; G02C 11/00; G02C 7/04; C08L 33/12
See application file for complete search history.

(56) References Cited

U.S. PATENT DOCUMENTS 9,028,772 B2 * 5/2015 Yao ..................... G03F 7/16
                                                    422/425
2008/0118399 A1 * 5/2008 Fleming ............. A61B 10/0045
                                                    422/68.1
(Continued)

OTHER PUBLICATIONS

Ruan, Jia-Li et al. "A Gelated Colloidal Crystal Attached Lens for Noninvasive Continuous Monitoring of Tear Glucose." Polymers vol. 9,4 125. Mar. 28, 2017, doi:10.3390/polym9040125 (Year: 2017).*

(Continued)

*Primary Examiner* — Eric J Messersmith
(74) *Attorney, Agent, or Firm* — ScienBiziP, P.C.

(57) ABSTRACT

An ophthalmic lens with glucose sensitive pad to indicate body glucose levels by changing color when in contact with tears from the eye includes a matrix, the matrix comprising a contact surface, the contact surface defining a micro-channel; and at least one glucose sensitive pad received in the micro-channel. A method for manufacturing an ophthalmic lens with glucose sensitive pad is also provided.

18 Claims, 3 Drawing Sheets

(51) Int. Cl.
*A61B 5/1468* (2006.01)
*A61B 10/00* (2006.01)
*G02C 11/00* (2006.01)
*G02B 1/04* (2006.01)
*B29B 13/08* (2006.01)
*B29D 11/00* (2006.01)
*G02C 7/04* (2006.01)

(52) U.S. Cl.
CPC ... *A61B 2562/0295* (2013.01); *A61B 2562/12* (2013.01); *B29D 11/00134* (2013.01)

(56) References Cited

U.S. PATENT DOCUMENTS

| | | | |
|---|---|---|---|
| 2012/0088258 A1* | 4/2012 | Bishop | A61B 5/14532 435/7.92 |
| 2012/0259188 A1* | 10/2012 | Besling | A61B 5/14507 600/319 |
| 2014/0088381 A1* | 3/2014 | Etzkorn | A61B 3/101 600/309 |

OTHER PUBLICATIONS

Wen-Jie Zhu, Da-Qian Feng, Meng Chen, Zhi-Dong Chen, Rong Zhu, Hai-Lin Fang, Wei Wang, Bienzyme colorimetric detection of glucose with self-calibration based on tree-shaped paper strip, Sensors and Actuators B: Chemical, vol. 190, (Year: 2014).*

* cited by examiner

OPHTHALMIC LENS WITH GLUCOSE SENSITIVE PAD AND METHOD FOR MANUFACTURING SAME

CROSS-REFERENCE TO RELATED APPLICATIONS

This application claims priority to Taiwanese Patent Application No. 106121876 filed on Jun. 30, 2017, the contents of which are incorporated by reference herein.

FIELD

The subject matter herein generally relates to ophthalmic lens.

BACKGROUND

Ophthalmic lens are commonly worn by users to correct vision, or for cosmetic or therapeutic reasons. An ophthalmic lens with ability to detect body glucose levels would be useful.

BRIEF DESCRIPTION OF THE DRAWINGS

Implementations of the present technology will now be described, by way of example only, with reference to the attached figures.

DETAILED DESCRIPTION

Figure 1:
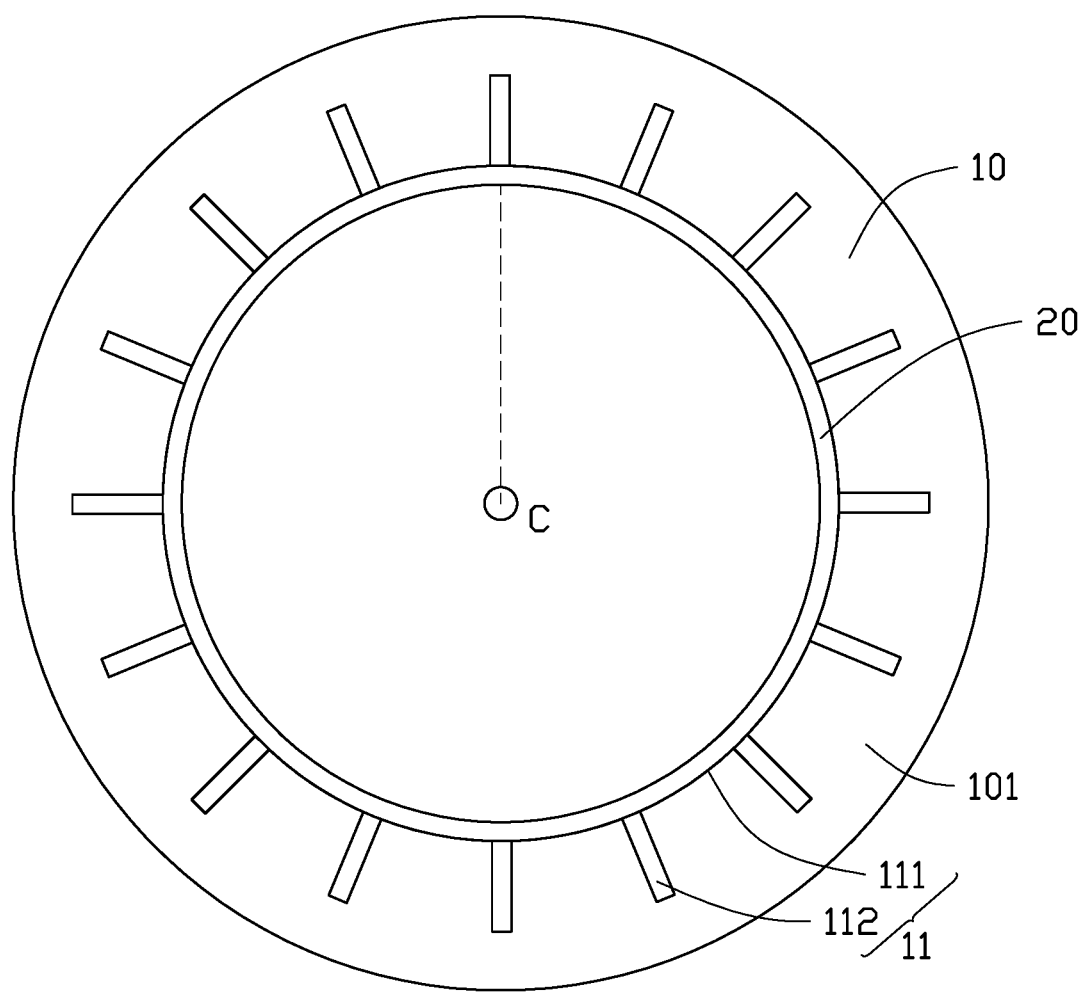
FIG. 1 is a top view of an ophthalmic lens according to an exemplary embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain sections have been exaggerated to better illustrate details and features of the present disclosure.

Several definitions that apply throughout this disclosure will now be presented.

The term "comprising," when utilized, means "including, but not necessarily limited to"; it specifically indicates open-ended inclusion or membership in the so-described combination, group, series, and the like.

Figure 2:
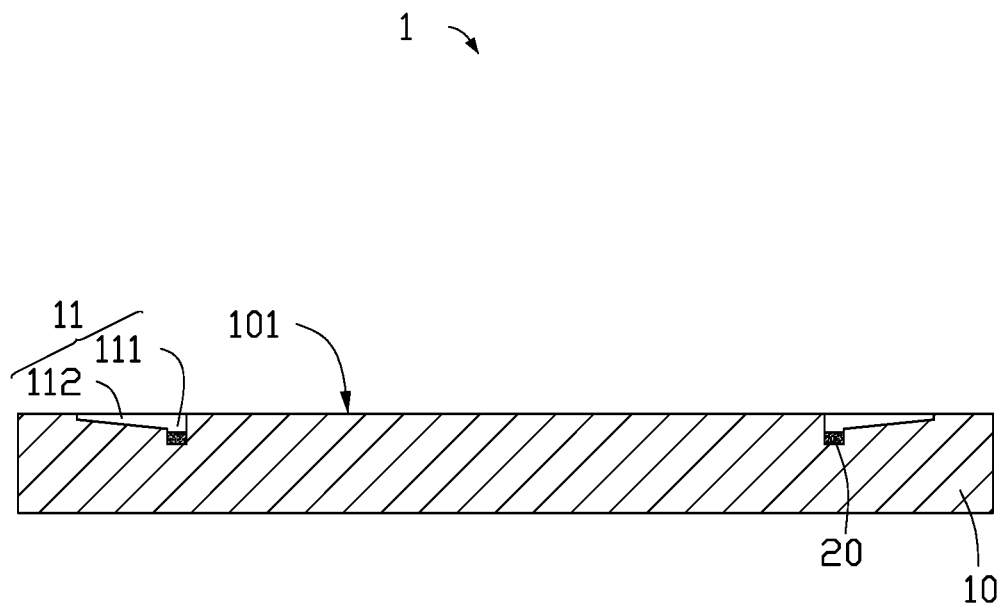
FIG. 2 is a cross-sectional view of the ophthalmic lens in FIG. 1.

FIGS. 1 and 2 illustrate an exemplary embodiment of an ophthalmic lens 1 including a matrix 10, and at least one glucose sensitive pad 20.

Preferably, the ophthalmic lens 1 is a rigid gas permeable contact lens. Preferably, the matrix 10 is made of polymethyl methacrylate (PMMA).

The matrix 10 includes a contact surface 101. The contact surface 101 defines a micro-channel 11. The micro-channel 11 can gather tears from the eye by capillary effect.

In this exemplary embodiment, the micro-channel 11 includes an annular groove 111 and a plurality of linear grooves 112. Each of the plurality of linear grooves 112 is in air communication with the annular groove 111.

Preferably, as shown in FIG. 1, a center of outer ring of the annular groove 111 and a center of inner ring of the annular groove 111 are coincident with a center C of the ophthalmic lens 1.

A width of the annular groove 111 can be in a range of 100 micrometers to 300 micrometers. A depth of the annular groove 111 can be in a range of about 250 micrometers to about 550 micrometers.

In this exemplary embodiment, each of the plurality of linear grooves 112 is extended along a perpendicular direction away from the annular groove 111.

Preferably, an extension line of each of the plurality of linear grooves 112 is coincident with the center of the ophthalmic lens 1.

A width of each of the plurality of linear grooves 112 can be in a range of about 100 micrometers to about 300 micrometers.

A depth of each of the plurality of linear grooves 112 is less than the depth of the annular groove 111.

Preferably, along a direction away from the annular groove 111, the depth of each of the plurality of linear grooves 112 decreases.

Preferably, a depth of an inner end portion of each linear groove 112 is in a range of about 100 micrometers to about 250 micrometers, and a depth of an outer end portion of each linear groove 112 away from the annular groove 111 is in a range of about 10 micrometers to about 100 micrometers.

The at least one glucose sensitive pad 20 is received in the micro-channel 11.

In this exemplary embodiment, there is one glucose sensitive pad 20. The glucose sensitive pad 20 is received in the annular groove 111, and is also annular shaped. The glucose sensitive pad 20 is formed by an injection molding process.

A width of the glucose sensitive pad 20 is substantially same as a width of the annular groove 111.

Preferably, a depth of the glucose sensitive pad 20 is less than a depth of the annular groove 111.

Preferably, the depth of the glucose sensitive pad 20 is in a range of about 80 micrometers to about 250 micrometers.

In other exemplary embodiments, the glucose sensitive pad 20 can also be received in the linear groove 112.

The glucose sensitive pad 20 can change color when in contact with glucose. The ophthalmic lens 1 can change color when worn by a wearer suffering from diabetes, for tears of diabetic patients always include glucose.

The glucose sensitive pad 20 is formed by polymerizing a glucose sensitive composite.

The glucose sensitive composite includes a gel pre-polymer, glucose oxidase (GOx), peroxidase, and a coloring agent.

The gel pre-polymer can be a hydrogel pre-polymer or a silicone hydrogel pre-polymer. In this exemplary embodiment, the gel pre-polymer is a hydrogel pre-polymer.

The hydrogel pre-polymer includes at least one hydrophilic monomer, at least one accelerant, and at least one crosslinking agent.

The hydrophilic monomer includes, but is not limited to, at least one acrylic-based monomer (CR'H=CRCOX), where R is H or CH3, R' is H, CH3 or alkali, X includes O, N, or one of the hydrophilic groups.

Preferably, the hydrophilic monomer is 2-hydroxyethyl methacrylate (HEMA), N-, N-dimethylacrylamide acrylamide (DMA), methacrylic acid (MAA), N-Vinylpyrrolidone (NVP), polyethylene glycol methacrylate (PEGMA), sulfobetaine methacrylate (SBMA), or a combination thereof.

The hydrophilic monomer can have a mass percentage of about 69.3% to about 99% of the total mass of the hydrogel pre-polymer.

Preferably, the hydrophilic monomer has a mass percentage of about 98% of the total mass of the hydrogel pre-polymer.

The accelerant is can be ammonium persulphate (SPS) and tetramethylethylenediamine (TEMED). The accelerant has a mass percentage of about 0.36% to about 19.5% of the total mass of the hydrogel pre-polymer.

Preferably, the accelerant has a mass percentage of about 1% of the total mass of the hydrogel pre-polymer.

The crosslinking agent can be ethylene glycol dimethacrylate (EGDMA), trimethylolpropane trimethacrylate (TMPTMA), N,N-Methylenebisacrylamide (MBAA), or a combination thereof. The crosslinking agent has a mass percentage of about 0.45% to about 12.8% of the total mass of the hydrogel pre-polymer.

Preferably, the crosslinking agent has a mass percentage of about 1% of the total mass of the hydrogel pre-polymer.

In other exemplary embodiments, the hydrogel pre-polymer can further include a solvent and additional agents.

A content of the glucose oxidase in the glucose sensitive composite can be in a range of about 62 active units per milliliter (unit/ML) to about 158 unit/ML.

Preferably, a content of the glucose oxidase in the glucose sensitive composite is about 85 unit/ML.

The peroxidase can be horseradish peroxidase.

A content of the peroxidase in the glucose sensitive composite can be in a range of about 16 unit/ML to about 204 unit/ML.

Preferably, a content of the peroxidase in the glucose sensitive composite is about 165 unit/ML.

The coloring agent can be 2,4,6-tribromo-3-hydroxybenzoic acid (TBHBA) and 4-amino antipyrine (4-AAP).

A content of the TBHBA in the glucose sensitive composite can be in a range of about 1.86 milligrams per milliliter (Mg/ML) to about 18.54 Mg/ML. A content of the 4-AAP in the glucose sensitive composite can be in a range of about 13.68 Mg/ML to about 42.2 Mg/ML.

Preferably, a content of the TBHBA in the glucose sensitive composite is about 5 Mg/ML, and a content of the 4-AAP in the glucose sensitive composite is about 20 Mg/ML.

In this exemplary embodiment, the glucose sensitive composite further includes photodegradable nano particles. A diameter of each photodegradable nano particle can be in a range of about 35 nanometers to about 250 nanometers. A content of the photodegradable nano particles in the glucose sensitive composite can be in a range of about 0.11 Mg/ML to about 8.6 Mg/ML.

Preferably, a content of the photodegradable nano particles in the glucose sensitive composite is about 5 Mg/ML.

In use, the linear grooves 112 and the annular groove 111 gather tears of a wearer by capillary effect. In this exemplary embodiment, tears gathered by the linear grooves 112 flow into the annular groove 111. Then, under an aerobic environment, glucose in the tears generates at least one oxide by the effect of the glucose oxidase in the glucose sensitive pad 20. Then, the coloring agent in the glucose sensitive pad 20 is oxidized by the at least one oxide and accordingly changes color, by the effect of the peroxidase in the glucose sensitive pad 20.

Figure 3:
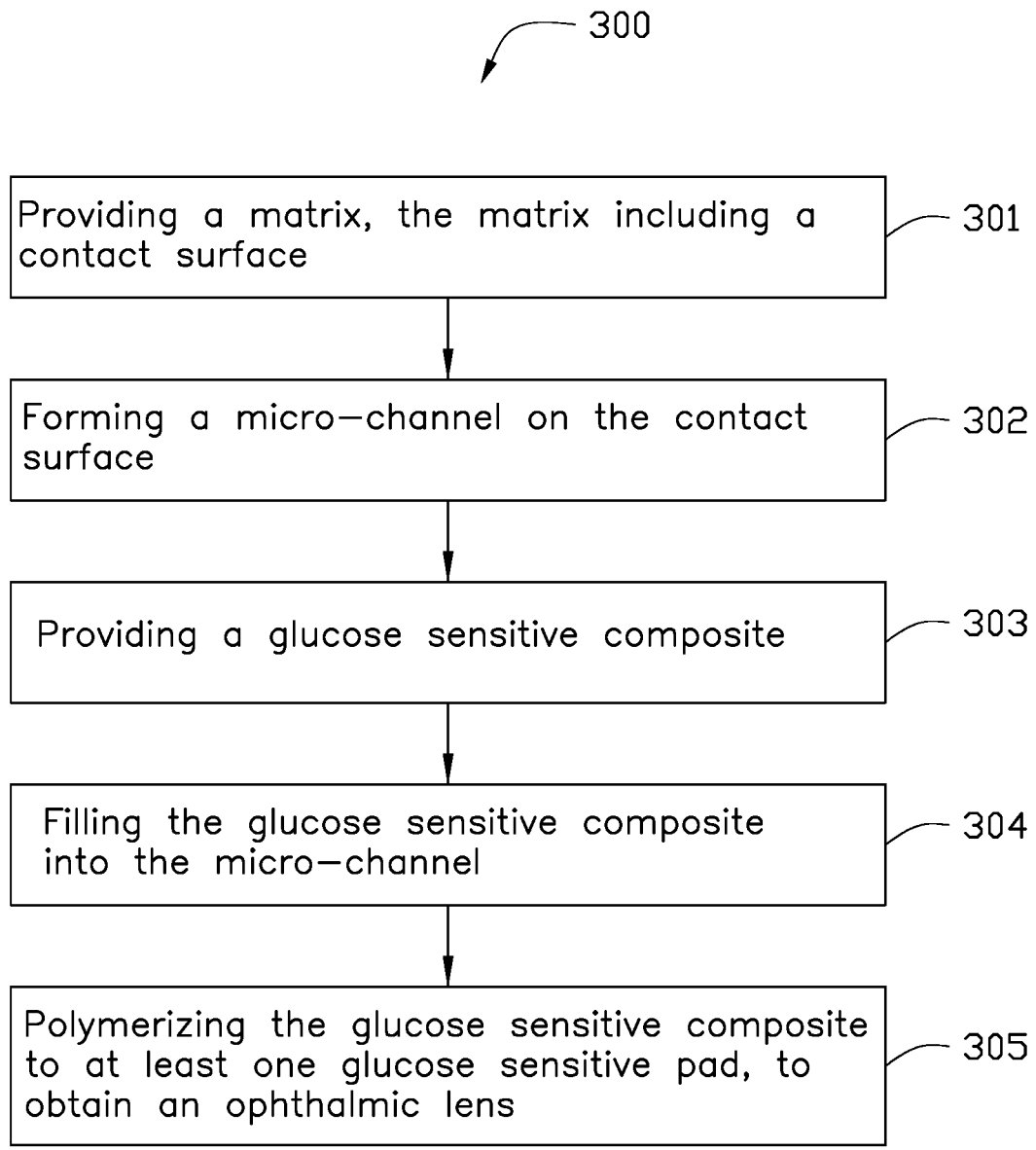
FIG. 3 is a flow chart of an exemplary embodiment of a method for manufacturing an ophthalmic lens.

Referring to the FIG. 3, a flowchart shows an example embodiment for a method for preparing an ophthalmic lens. An example method 300 is provided by way of example, as there are a variety of ways to carry out the method. The method 300 described below can be carried out using the configurations illustrated in the figure, for example, and various elements of these figures are referenced in explaining example method 300. Each block shown in the figure represents one or more processes, methods, or subroutines, carried out in the exemplary method 300. Additionally, the illustrated order of blocks is by example only and the order of the blocks can change. The exemplary method 300 can begin at block 301.

At block 301, a matrix is provided. The matrix includes a contact surface.

At block 302, a micro-channel is formed on the contact surface of the matrix.

At block 303, a glucose sensitive composite is provided.

At block 304, the glucose sensitive composite is filled into the micro-channel.

At block 305, the glucose sensitive composite is polymerized to be at least one glucose sensitive pad, to obtain an ophthalmic lens.

At block 301, as illustrate in FIGS. 1 and 2, the matrix 10 includes a contact surface 101.

Preferably, the matrix 10 is made of polymethyl methacrylate (PMMA).

At block 302, the micro-channel can be formed by a laser cutting process.

As illustrate in FIGS. 1 and 2, the micro-channel 11 includes an annular groove 111 and a plurality of linear grooves 112. Each of the plurality of linear grooves 112 is in air communication with the annular groove 111.

Preferably, a center of outer ring of the annular groove 111 and a center of inner ring of the annular groove 111 are coincident with a center of the ophthalmic lens 1.

A width of the annular groove 111 can be in a range of about 100 micrometers to about 300 micrometers. A depth of the annular groove 111 can be in a range of about 250 micrometers to about 550 micrometers.

In this exemplary embodiment, each of the plurality of linear grooves 112 is extended along a direction away from the annular groove 111.

Preferably, an extension line of each of the plurality of linear grooves 112 is coincident with the center of the ophthalmic lens 1.

A width of each of the plurality of linear grooves 112 can be in a range of about 100 micrometers to about 300 micrometers.

A depth of each of the plurality of linear grooves 112 is less than the depth of the annular groove 111.

Preferably, along a direction away from the annular groove 111, the depth of each of the plurality of linear grooves 112 decreases.

Preferably, a depth of an inner end portion of each linear groove 112 is in a range of about 100 micrometers to about 250 micrometers, and a depth of an outer end portion of each linear groove 112 away from the annular groove 111 is in a range of about 10 micrometers to about 100 micrometers.

The glucose sensitive composite includes a gel pre-polymer, a glucose oxidase (GOx), a peroxidase, and a coloring agent.

The gel pre-polymer can be a hydrogel pre-polymer or a silicone hydrogel pre-polymer. In this exemplary embodiment, the gel pre-polymer is a hydrogel pre-polymer.

The hydrogel pre-polymer includes at least one hydrophilic monomer, at least one accelerant, and at least one crosslinking agent.

The hydrophilic monomer includes, but is not limited to, at least one acrylic-based monomer (CR'H'CRCOX), where R is H or CH3, R' is H, CH3 or alkali, X includes O, N, or one of the hydrophilic groups.

Preferably, the hydrophilic monomer is 2-hydroxyethyl methacrylate (HEMA), N-, N-dimethylacrylamide acrylamide (DMA), methacrylic acid (MAA), N-Vinylpyrrolidone (NVP), polyethylene glycol methacrylate (PEGMA), sulfobetaine methacrylate (SBMA), or a combination thereof.

The hydrophilic monomer can has a mass percentage of about 69.3% to about 99% of the total mass of the hydrogel pre-polymer.

Preferably, the hydrophilic monomer has a mass percentage of about 98% of the total mass of the hydrogel pre-polymer.

The accelerant is can be ammonium persulphate (SPS) and tetramethylethylenediamine (TEMED). The accelerant has a mass percentage of about 0.36% to about 19.5% of the total mass of the hydrogel pre-polymer.

Preferably, the accelerant has a mass percentage of about 1% of the total mass of the hydrogel pre-polymer.

The crosslinking agent can be ethylene glycol dimethacrylate (EGDMA), trimethylolpropane trimethacrylate (TMPTMA), N,N'-Methylenebisacrylamide (MBAA), or a combination thereof. The crosslinking agent has a mass percentage of about 0.45% to about 12.8% of the total mass of the hydrogel pre-polymer.

Preferably, the crosslinking agent has a mass percentage of about 1% of the total mass of the hydrogel pre-polymer.

In other exemplary embodiments, the hydrogel pre-polymer can further include a solvent, and additional agents.

A content of the glucose oxidase in the glucose sensitive composite can be in a range of 62 about active units per milliliter (unit/ML) to about 158 unit/ML.

Preferably, a content of the glucose oxidase in the glucose sensitive composite is 85 unit/ML.

The peroxidase can be horseradish peroxidase.

A content of the peroxidase in the glucose sensitive composite can be in a range of 16 unit/ML to 204 unit/ML.

Preferably, a content of the peroxidase in the glucose sensitive composite is 165 unit/ML.

The coloring agent can be 2,4,6-tribromo-3-hydroxybenzoic acid (TBHBA) and 4-amino antipyrine (4-AAP).

A content of the TBHBA in the glucose sensitive composite can be in a range of about 1.86 milligrams per milliliter (Mg/ML) to about 18.54 Mg/ML. A content of the 4-AAP in the glucose sensitive composite can be in a range of about 13.68 Mg/ML to about 42.2 Mg/ML.

Preferably, a content of the TBHBA in the glucose sensitive composite is about 5 Mg/ML, and a content of the 4-AAP in the glucose sensitive composite is about 20 Mg/ML.

In this exemplary embodiment, the glucose sensitive composite further includes photodegradable nano particles. A diameter of each photodegradable nano particle can be in a range of about 35 nanometers to about 250 nanometers. A content of the photodegradable nano particles in the glucose sensitive composite can be in a range of about 0.11 Mg/ML to about 8.6 Mg/ML.

Preferably, a content of the photodegradable nano particles in the glucose sensitive composite is about 5 Mg/ML.

In this exemplary embodiment, the glucose sensitive composite is filled into the annular groove 111.

In other exemplary embodiments, the glucose sensitive composite can also be filled into the linear groove 112.

The glucose sensitive composite can be polymerized under ultraviolet or heat.

In this exemplary embodiment, the glucose sensitive composite is polymerized under ultraviolet with a wavelength in about 420 nanometers for about 5 minutes.

In this exemplary embodiment, as illustrate in FIGS. 1 and 2, there is one glucose sensitive pad 20. The glucose sensitive pad 20 is received in the annular groove 111, and is also annular shaped.

A width of the glucose sensitive pad 20 is substantially same as a width of the annular groove 111.

Preferably, a depth of the glucose sensitive pad 20 is less than a depth of the annular groove 111.

Preferably, the depth of the glucose sensitive pad 20 is in a range of about 80 micrometers to about 250 micrometers.

EXAMPLE 1

A method for preparing an ophthalmic lens includes the following steps.

A matrix is provided. The matrix includes a contact surface.

A micro-channel is formed on the contact surface of the matrix. The micro-channel includes an annular groove and a plurality of linear grooves. Each of the plurality of linear grooves is in air communication with the annular groove. A depth of each of the plurality of linear grooves is less than the depth of the annular groove.

A glucose sensitive composite is provided. The glucose sensitive composite includes a gel pre-polymer, a glucose oxidase, a peroxidase, a coloring agent and photodegradable nano particles. The hydrophilic monomer includes HEMA, EGDMA, APS and TEMEA. The HEMA has a mass percentage of about 98% of the total mass of the hydrogel pre-polymer. The EGDMA has a mass percentage of about 1% of the total mass of the hydrogel pre-polymer. The APS and the TEMEA has a total mass percentage of about 1% of the total mass of the hydrogel pre-polymer. The peroxidase can be horseradish peroxidase. A content of the horseradish peroxidase in the glucose sensitive composite is about 165 unit/ML. The coloring agent is 2,4,6-tribromo-3-hydroxybenzoic acid (TBHBA) and 4-amino antipyrine (4-AAP). A content of the TBHBA in the glucose sensitive composite is about 5 Mg/ML, and a content of the 4-AAP in the glucose sensitive composite is about 20 Mg/ML. A content of the photodegradable nano particles in the glucose sensitive composite is about 5 Mg/ML.

The glucose sensitive composite is filled into the micro-channel and is polymerized under ultravioletto be a glucose sensitive pad, to obtain an ophthalmic lens.

EXAMPLE 2

An ophthalmic lens 1 formed by method of example 1. The ophthalmic lens includes a matrix and a glucose sensitive pad. The matrix includes a contact surface. The contact surface defines a micro-channel. The micro-channel includes an annular groove and a plurality of linear grooves. Each of the plurality of linear grooves is in air communication with the annular groove. A depth of each of the plurality of linear grooves is less than the depth of the annular groove. The glucose sensitive pad receives in the annular groove.

Detecting the ophthalmic lens in example 2 by putting the ophthalmic lens into a glucose solution and observing a color of the ophthalmic lens, and it can be seen that the color of the ophthalmic lens is changed from colorless to red.

Glucose is detected in the ophthalmic lens in example 2 by a spectrometer.

The exemplary embodiments shown and described above are only examples. Many details are often found in the art such as the other features of an intraocular lens 3. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size, and arrangement of the sections within the principles of the present disclosure, up to and including the full extent established by the broad general meaning of the terms used in the claims. It will therefore be appreciated that the exemplary embodiments described above may be modified within the scope of the claims.

What is claimed is:

1. An ophthalmic lens with glucose sensitive pad, comprising:
   a matrix, the matrix comprising a contact surface, the contact surface defining a micro-channel; and
   at least one glucose sensitive pad received in the micro-channel
   wherein the micro-channel comprises an annular groove and a plurality of linear grooves; each of the plurality of linear grooves is in air communication with the annular groove.

2. The ophthalmic lens with glucose sensitive pad of claim 1, wherein the matrix is made of polymethyl methacrylate.

3. The ophthalmic lens with glucose sensitive pad of claim 1, wherein each of the plurality of linear grooves is extended along a direction away from the annular groove.

4. The ophthalmic lens with glucose sensitive pad of claim 1, wherein a depth of each of the plurality of linear grooves is less than the depth of the annular groove.

5. The ophthalmic lens with glucose sensitive pad of claim 4, wherein along a direction away from the annular groove, the depth of each of the plurality of linear grooves decreases.

6. The ophthalmic lens with glucose sensitive pad of claim 5, wherein a depth of an inner end portion of each linear groove is in a range of about 100 micrometers to about 250 micrometers; a depth of an outer end portion of each linear groove away from the annular groove is in a range of about 10 micrometers to about 100 micrometers; a depth of the annular groove is in a range of about 250 micrometers to about 550 micrometers.

7. The ophthalmic lens with glucose sensitive pad of claim 6, wherein a depth of the glucose sensitive pad is in a range of about 80 micrometers to about 250 micrometers.

8. The ophthalmic lens with glucose sensitive pad of claim 1, wherein the glucose sensitive pad comprises glucose oxidase, peroxidase, and a coloring agent.

9. The ophthalmic lens with glucose sensitive pad of claim 8, wherein the peroxidase is horseradish peroxidase.

10. The ophthalmic lens with glucose sensitive pad of claim 8, wherein the coloring agent is 2,4,6-tribromo-3-hydroxybenzoic acid and 4-amino antipyrine.

11. A method for manufacturing an ophthalmic lens, comprising:
    providing a matrix, the matrix comprising a contact surface;
    forming a micro-channel on the contact surface, wherein the micro-channel comprises an annular groove and a plurality of linear grooves; each of the plurality of linear grooves is in air communication with the annular groove;
    providing a glucose sensitive composite;
    filling the glucose sensitive composite into the micro-channel; and
    polymerizing the glucose sensitive composite to at least one glucose sensitive pad, to obtain an ophthalmic lens.

12. The method of claim 11, wherein the micro-channel is formed by a laser cutting process.

13. The method of claim 11, wherein the glucose sensitive composite comprises a gel pre-polymer, a glucose oxidase, a peroxidase, and a coloring agent; and wherein the gel pre-polymer is a hydrogel pre-polymer or a silicone hydrogel pre-polymer.

14. The method of claim 13, wherein the gel pre-polymer is a hydrogel pre-polymer, the hydrogel pre-polymer comprising at least one hydrophilic monomer, at least one accelerant, and at least one crosslinking agent.

15. The method of claim 13, wherein a content of the glucose oxidase in the glucose sensitive composite is in a range of about 62 active units per milliliter (unit/ML) to about 158 unit/ML.

16. The method of claim 13, wherein a content of the peroxidase in the glucose sensitive composite is in a range of about 16 unit/ML to about 204 unit/ML.

17. The method of claim 13, wherein the coloring agent is 2,4,6-tribromo-3-hydroxybenzoic acid (TBHBA) and 4-amino antipyrine (4-AAP); a content of the TBHBA in the glucose sensitive composite is in a range of about 1.86 milligrams per milliliter (Mg/ML) to about 18.54 Mg/ML; a content of the 4-AAP in the glucose sensitive composite is in a range of about 13.68 Mg/ML to about 42.2 Mg/ML.

18. The method of claim 13, wherein the glucose sensitive composite further comprises photodegradable nano particles, a content of the photodegradable nano particles in the glucose sensitive composite is in a range of about 0.11 Mg/ML to about 8.6 Mg/ML.

* * * * *